United States Patent [19]

Best et al.

[11] 4,132,773
[45] Jan. 2, 1979

[54] DENTIFRICES

[75] Inventors: John S. Best, Camberley; Ronald Hoyles, Epsom Downs; Geoffrey S. Ingram, West Wickham; Francis B. J. Skinner, Yateley near Camberley, all of England

[73] Assignee: Lever Brothers Company, New York, N.Y.

[21] Appl. No.: 798,094

[22] Filed: May 18, 1977

[30] Foreign Application Priority Data

May 19, 1976 [GB] United Kingdom ............... 20702/76

[51] Int. Cl.$^2$ ............................................... A61K 7/16
[52] U.S. Cl. .......................................... 424/57; 424/49
[58] Field of Search ..................................... 424/49–58

[56] References Cited

U.S. PATENT DOCUMENTS

| | | | |
|---|---|---|---|
| 3,538,230 | 11/1970 | Pader et al. | 424/50 |
| 3,662,059 | 5/1972 | Wiesner et al. | 424/52 |
| 3,689,637 | 9/1972 | Pader | 424/52 |
| 3,699,220 | 10/1972 | Weststrate et al. | 424/52 |
| 3,927,202 | 12/1975 | Harvey et al. | 424/57 |

OTHER PUBLICATIONS

Gonzalez et al., J. Dent. Res. 52(2): 261–266 (1973) "Trimetaphosphate and Fluoride Actions on Mineralization at the Enamel-Solution Interface."

Gonzalez, J. Dent. Res. 50:1056–1064 (1971), "Effect of Trimetaphoshate Ions on the Process of Mineralization."

Navia et al., J. Dent. Res. 48:183–191, Apr. 1969, "Longitudinal Study of Cariostatic Effects of Sodium Trimetaphosphate and Sodium Fluoride When Fed Separately and Together in Diets of Rats."

Navia et al., Dental Abstracts 14:208–209, Apr. 1969, "Cariostatic Effects of Sodium Trimetaphosphate."

*Primary Examiner*—Shep K. Rose
*Attorney, Agent, or Firm*—Kenneth F. Dusyn; James J. Farrell; Melvin H. Kurtz

[57] ABSTRACT

Dentifrice composition for combatting dental caries containing sodium trimetaphosphate as an anti-caries agent and a compatible abrasive agent comprising a silica xerogel.

2 Claims, No Drawings

DENTIFRICES

This invention relates to dentifrices and more particularly to those containing anti-caries agents.

Amongst a number of anti-cariogenic substances that have been suggested for use in dentifrices there has recently been suggested in UK Patent Specification No. 1,275,816 the use of the combination of sodium monofluorophosphate and sodium trimetaphosphate.

The present invention is based on our discovery that sodium trimetaphosphate is particularly compatible with silica xerogel abrasives and that a dentifrice utilising a silica xerogel as an abrasive and containing sodium trimetaphosphate is effective in reducing dental caries.

Accordingly therefore the present invention provides a dentifrice for combatting dental caries comprising from 0.5 to 6%, preferably 1 to 5%, by weight of sodium trimetaphosphate and a silica xerogel abrasive.

Silica xerogel abrasives are a known class of dentifrice abrasives and have been described for instance in U.S. Pat. Nos. 3,538,230 and 3,689,637, and UK Patent Specification No. 1,419,692. Preferred silica xerogels are those having an average particle size of from about 2 to about 30 microns. While the amount of the silica xerogel abrasive in the dentifrices of the invention may range from 0.5% to 95% by weight the preferred amount for dentifrices in the form of creams or pastes is from about 5% to about 50% by weight.

The dentifrices may also contain resin abrasives, such as those described in UK Patent Specification No. 1,419,692. A proportion of insoluble sodium metaphosphate may also be included to supplement the abrasive action of the silica xerogel cleansing agent.

The dentifrices of the invention may also contain other anti-caries agents, especially sodium monofluorophosphate, in an amount of from 0.2 to 8% by weight, preferably 0.5 to 2.5% by weight.

The pH of the dentifrices of the invention is desirably from about 6 to about 8 in which range sodium trimetaphosphate has good stability.

The dentifrices of the invention may also contain the usual ingredients such as humectant, binder or thickening agent, surface active agent, flavouring agent, and sweetening agent, for example those described in the above-mentioned patent specifications.

Toothpastes were made having the composition given in Table 1, the amounts of the ingredients being percentages by weight. Examples I to V are according to the invention and Examples A to C are given for comparative purposes.

TABLE 1

| Ingredient | I | II | III | IV | V | A | B | C |
|---|---|---|---|---|---|---|---|---|
| Silica xerogel (Gasil 200) | 10.0 | 13.0 | 10.0 | 13.0 | 13.0 | | | |
| Silica aerogel (Gasil 23) | 11.0 | 6.0 | 11.0 | 6.0 | 6.0 | | | |
| Hydrated alumina | | | | | | 50.0 | 45.0 | |
| Dicalcium phospate dihydrate | | | | | | | | 31.0 |
| Chalk | | | | | | | | 12.0 |
| Sodium dihydrogen phosphate | | | | | | 0.5 | 0.5 | |
| Sorbitol (70%) | 40.0 | | 40.0 | | | 27.0 | 27.0 | 27.0 |
| Glycerol | | 35.0 | | 35.0 | 35.0 | | | |
| Titanium dioxide | 1.0 | 0.5 | 1.0 | 0.5 | 0.5 | 1.0 | 1.0 | |
| Sodium carboxymethylcellulose | 0.4 | | 0.4 | | | | | |
| Sodium caragheenate | | 1.6 | | 1.6 | 1.6 | 1.0 | 1.0 | 1.0 |
| Sodium N-lauroyl sarcosinate (30%) | 6.7 | 6.7 | | | 6.7 | 6.7 | 6.7 | 3.3 |
| Sodium lauryl sulphate | | | 1.5 | 1.5 | | | | |
| Polyethylene glycol | 5.0 | | 5.0 | | | | | |
| Saccharin | 0.2 | 0.2 | 0.2 | 0.2 | 0.2 | 0.2 | 0.2 | 0.3 |
| Flavour | 1.0 | 1.0 | 1.0 | 1.0 | 1.0 | 1.0 | 1.0 | 1.0 |
| Sodium trimetaphosphate | 3.0 | 3.0 | 3.0 | 3.0 | 1.0 | 3.0 | 3.0 | 1.0 |
| Water | ← to 100.0 → | | | | | | | |

Data for analysis for sodium trimetaphosphate after various periods of storage are given in Table 2.

TABLE 2

Analysis for Sodium Trimetaphosphate after Storage

| Toothpaste | Months at 15° C | | | | | | Months at 37° C | | | | | | 2 weeks at room temp (22° C) |
|---|---|---|---|---|---|---|---|---|---|---|---|---|---|
| | 1 | 2 | 3 | 4 | 5 | 6 | 1 | 2 | 3 | 4 | 5 | 6 | |
| I | 3.0 | 2.8 | — | 2.8 | 2.9 | 3.0 | 3.0 | 2.3 | 2.3 | 2.1 | 1.7 | 1.6 | — |
| II | 2.6 | — | 2.6 | 2.8 | — | — | 2.6 | — | 2.6 | 2.3 | — | — | — |
| III | 3.2 | 3.2 | 3.0 | 3.0 | — | — | 3.0 | 2.9 | 2.4 | 2.3 | — | — | — |
| V | 0.9 | 0.6 | 0.8 | 0.7 | — | — | 0.8 | 0.6 | 0.8 | 0.8 | — | — | — |
| A | — | — | — | 1.3 | 0.9 | 0.8 | — | — | — | 0.0 | 0.0 | — | — |
| B | — | — | — | 1.7 | 1.5 | 1.4 | — | — | — | 0.0 | 0.0 | — | — |
| C | — | — | — | — | — | — | — | — | — | — | — | — | 0.6 |

These data show that toothpastes containing silica xerogel as abrasive retain higher levels of sodium trimetaphosphate compared with toothpastes based on hydrated alumina abrasives. The data also show that toothpastes containing as abrasive a mixture of dicalcium phosphate dihydrate and calcium carbonate are poor at retaining sodium trimetaphosphate.

In tests on rats, toothpastes containing sodium trimetaphosphate and silica xerogel, without any other anti-caries agent present, have been shown to be effective in reducing dental caries. The percentage reductions in carious lesions compared to the placebo paste which did not contain sodium trimetaphosphate are given below in Table 3.

TABLE 3

| Toothpaste | Number of Rats in Test | Percentage Reduction in Carious Lesions | Mean Value* |
|---|---|---|---|
| I | 20 | 12 | |
| I | 14 | 17 | 14 |
| II | 18 | 67 | |
| II | 14 | 50 | 58 |
| II | 14 | 54 | |

TABLE 3-continued

| Toothpaste | Number of Rats in Test | Percentage Reduction in Carious Lesions | Mean Value* |
|---|---|---|---|
| III | 14 | 51 | 51 |
| IV | 18 | 77 | 77 |

*This takes into account the number of animals in the tests.

What is claimed is:

1. An improved dentifrice composition effective against dental caries comprising
   (a) from about 0.5 to about 6% by weight of sodium trimetaphosphate as an anti-caries agent; and
   (b) from about 0.5 to about 95% by weight of a silica xerogel as an abrasive cleaning agent having an average particle size of about 2 to about 30 microns; the percentages being based on the total weight of the composition.

2. The dentifrice composition of claim 1 which is in the form of a toothpaste and wherein the silica xerogel is present in an amount of from about 5% to about 50% by weight.